United States Patent [19]

Tomiyama

[11] Patent Number: 4,584,292
[45] Date of Patent: Apr. 22, 1986

[54] ANTIHYPERTENSIVE 1,5-BENZOTHIAZEPINE DERIVATIVES AND COMPOSITIONS THEREOF

[75] Inventor: Tsuyoshi Tomiyama, Sakaki, Japan

[73] Assignee: Kotobuki Seiyaku Co., Ltd., Sakaki, Japan

[21] Appl. No.: 662,840

[22] Filed: Oct. 19, 1984

[51] Int. Cl.$^4$ .................. A61K 31/55; A61K 31/44; C07D 285/36; C07D 417/06
[52] U.S. Cl. ............................ 514/211; 546/270; 546/200; 260/330; 260/239 A; 544/359; 548/336; 548/524
[58] Field of Search ............... 546/270, 272; 260/330; 514/211

[56] References Cited
FOREIGN PATENT DOCUMENTS
0211289 6/1984 Japan .................. 260/330

*Primary Examiner*—Henry R. Jiles
*Assistant Examiner*—J. G. Mullins
*Attorney, Agent, or Firm*—Robert E. Burns; Emmanuel J. Lobato; Bruce L. Adams

[57] ABSTRACT

A series of new 1,5-benzothiazepine analogues are disclosed.

These new compounds are represented by the following general formula:

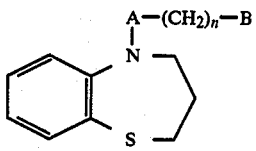

wherein :
A is $>C=O$ or $>CH_2$,
n is an integer from 1 to 3,
B is

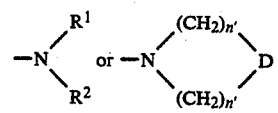

wherein $R^1$ represents H, alkyl or acyl group; $R^2$ is

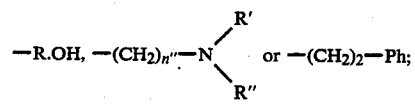

D represents

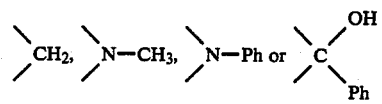

wherein n' and n" each represents 1 or 2. R, R', R" each represents a lower alkyl, Ph represents phenyl group or a substituted phenyl group.

The compounds of the present invention are useful as hypertensive agents.

17 Claims, 1 Drawing Figure

ANTIHYPERTENSIVE 1,5-BENZOTHIAZEPINE DERIVATIVES AND COMPOSITIONS THEREOF

BACKGROUND OF THE INVENTION

This invention relates to new 1,5-benzothiazepine derivatives, therapeutic compositions containing these derivatives and the method of manufacturing the same.

SUMMARY OF THE INVENTION

The principal object of the present invention is the provision of novel compounds having advantageous pharmaceutical properties.

Another object of the present invention is the provision of pharmaceutical compositions useful as antihypertensive agents.

Still another object of the present invention is the provision of new 1,5-benzothiazepine derivatives and a method for the manufacture thereof.

These and other objects of the invention will become apparent from the description that follows.

DETAILED DESCRIPTION OF THE INVENTION

Figure 1:
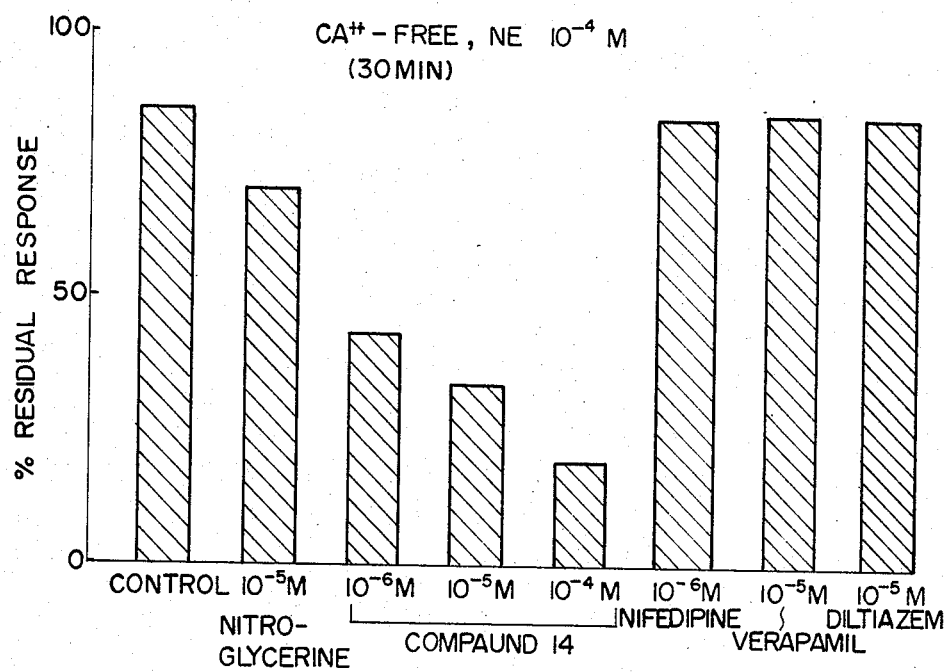

This invention relates to new 1,5-benzothiazepine derivatives and their acid-addition salts, and a method of their synthesis and use as potent anti-hypertensive agents.

The compounds of this invention are represented by the general formula (I):

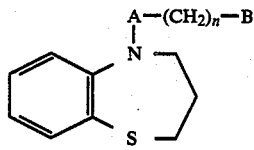

wherein:
A is $>C=O$ or $>CH_2$,
n is an integer from 1 to 3,
B is

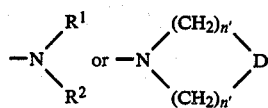

wherein $R^1$ represents H, an alkyl or acyl group,; $R^2$ is

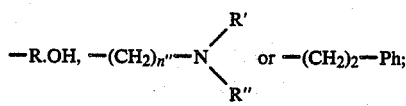

D represents

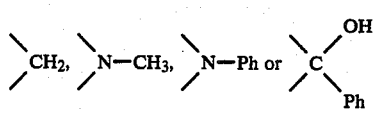

wherein n' and n'' each represents 1 or 2. R, R', R'' each represents a lower alkyl, Ph represents phenyl group or a substituted phenyl group.
and their acid-addition salts.

The acyl group indicated at $R^1$ is, for example, an acetyl, propionyl or benzoyl groups.

The hydroxy lower alkyl of the symbol $R^2$ is 2-hydroxypropyl or 2-hydroxy-1,1-dimethylethyl.

In case $R^2$ is

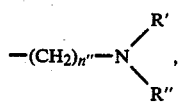

they are, for example, dimethylaminopropyl, and diethylaminoethyl.

Among the heterocyclic compounds represented by symbol B are N-methylpiperazino, N-phenylpiperazino or 4-(P-chlorophenyl)-4-hydroxypiperidino groups.

The compounds related to the general formula (I) are as follows.

| comp. No. | A | $(CH_2)_n-$ | B |
|---|---|---|---|
| 1 | $\diagdown C=O \diagup$ | $-CH_2-$ | $-NH-CH_2CH(OH)(CH_3)$ |
| 2 | $\diagdown C=O \diagup$ | $-CH_2-$ | $-NH-C(CH_3)_2-CH_2OH$ |
| 3 | $\diagdown C=O \diagup$ | $-CH_2-$ | piperidino |
| 4 | $\diagdown C=O \diagup$ | $-CH_2-$ | $-NH-$ (6-methylpyridin-2-yl) |
| 5 | $\diagdown C=O \diagup$ | $-CH_2-$ | $-N(CH(CH_3)_2)_2$ |
| 6 | $\diagdown C=O \diagup$ | $-CH_2-$ | $-NH-Ph$ |
| 7 | $\diagdown C=O \diagup$ | $-CH_2-$ | $-NH-(CH_2)_3-N(CH_3)_2$ |

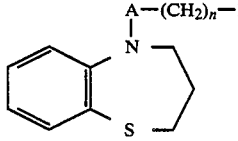

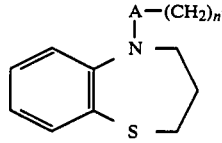

The compounds of the general formula (I) can be prepared by the procedure of the present invention, and the first step is to react 2,3,4,5-tetrahydro-1,5 benzothiazepine the formula (II) with a compound of the formula (III) to give a compound of the general formula (IV).

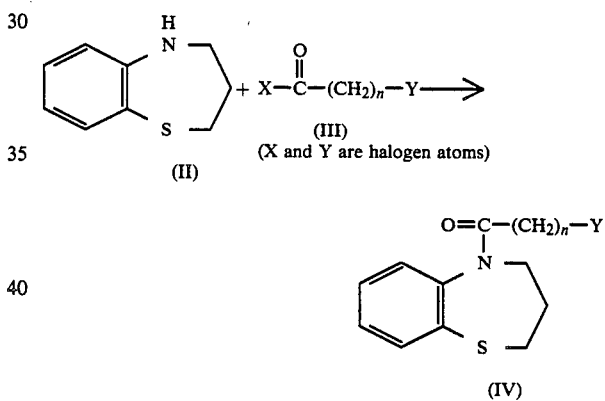

The second step comprises reacting a compound of the general formula (IV) with a compound of the formula (V)

wherein Z is

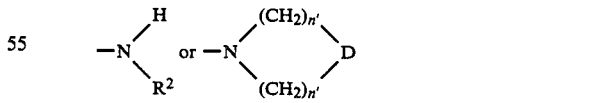

and other symbols are same as defined before, to give a compound of the general formula (VI).

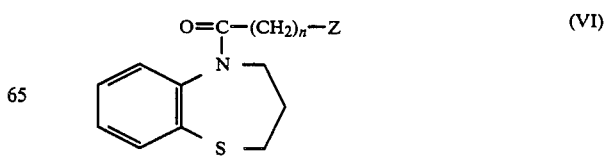

The compound of the formula (II), 2,3,4,5-tetrahydro-1,5-benzothiazepine can be prepared according to the procedures of dibenzothiazepine described by H. L. Yale et al (Jour. Heterocycle. chem. 1972, 9, 899), replacing α,γ-dibromopropane to O-aminothiophenol.

Alternatively, it can be obtained by reacting benzothiazole with 1,3-dibromopropane according to the method of H. J. Federsel (Tetrahedron. Lett. 21, 2429P. 1980). The compounds represented by the general gormula (III) are, for example, chloroacetyl chloride, bromoacetyl-bromide, 2-chloropropionyl chloride, and 3-chlorobutyryl chloride. The reaction of compounds (II) and (III) can be carried out in an inert solvent like benzene or toluene, but preferentially is carried out in a basic solvent such as triethylamine or pyridine. The reaction of compounds (IV) and (V) requires a base or a biequivalent amount of compound (V). As to the base required in this reaction, a compound such as triethylamine, pyridine, potassium carbonate, sodium ethylate, sodium amide and sodium hydride may be employed.

In the case of Z being —NH—ROH in the general formula (V), 2-hydroxypropylamine, 2-hydroxy-1,1-dimethylethylamine and diisopropylamine can be mentioned as examples. When Z is

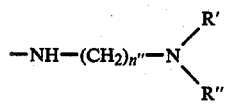

dimethylaminopropylamine and diethylaminoethylamine may be exemplified. When Z is —NH—(CH$_2$)$_n$″—NH—CH$_2$CH$_2$—Ph, 4-methoxyphenethylamine and 3,4-dimethoxyphenethylamine may be exemplified. Moreover, when Z is a heterocyclic compound, N-methylpiperazine, N-phenylpiperazine, 4-phenyl-4-hydroxypiperidine and 4-P-chlorophenyl-4-hydroxypiperidine may be examples in point. The compounds of the general formula (VII) are obtained by reducing a compound

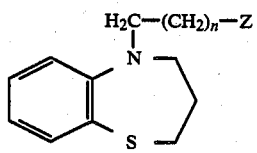 (VII)

of the general formula (VI), using a reducing agent such as lithium aluminum hydride or sodium boron hydride. Ordinary acylation can be applied to react a compound of the general formula (VI) in the case of Z being

with a compound of the general formula (VIII)

 (VIII)

R$^{1'}$ is acyl, X is halogen atom.
to give a compound of the general formula (IX).

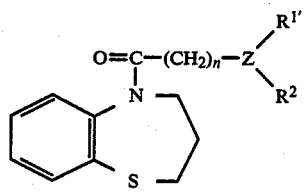

The compounds of the general formula (I) and their pharmacologically acceptable acid-addition salts are therapeutically active compounds. Thus the compounds of the invention can be administered both perorally and parenterally in the form of tablets, capsules, granules, suppositories and injections. Doses to be administered to particular patients are various, depending on the patient's condition, patient's response or age. One effective dosage unit of the compound according to the present invention is from 100 mg to 250 mg for an adult, three times a day. The following example illustrates pharmacological data, a few pharmaceutical dosage unit compositions method of preparation thereof and procedures for preparing the active compounds.

PHARMACOLOGICAL EXPERIMENT 1

Ca$^{++}$—antagonistic activity

Guinea-pig taenia cecum is isolated and suspended in a bath for 30 minutes. The normal-Ringer solution is then replaced by K$^+$—Ringer. In this condition, taenia cecum is contracted by elevating Ca$^{++}$—ion concentration of K$^+$—Ringer. Pretreatment by the compound of this invention inhibits this contraction. The potency of this inhibition is expressed as PA$_2$ value (Table 2). Experiments are carried out according to M. Ferrari (Arch. Intern. Pharmacodyn. 174, 223-318 (1968)).

TABLE 2

| Compound No. | PA$_2$ value |
|---|---|
| No. 1 | 6.77 |
| No. 14 | 6.23 |
| No. 16 | 6.72 |
| No. 19 | 6.72 |

PHARMACOLOGICAL EXPERIMENT 2

The coronary artery dilating activity of the compounds is estimated by Rangendorf method (Pflugers. Arch. Ges. Physiol. 61, 291 (1895)) using the isolated guinea-pig heart. The maximum increased coronary blood flow and its increase % to control values are summarized in Table 3.

TABLE 3

| Compound No. | concentration (μg/heart) | maximum increased blood flow | increase (%) |
|---|---|---|---|
| 1 | 30 | 25.1 ± 3.5 | 53.1 ± 16.1 |
| 14 | 30 | 10.4 ± 6.8 | 20.2 ± 4.0 |
| 16 | 100 | 33.1 ± 8.1 | 37.6 ± 7.2 |
| 19 | 30 | 11.8 ± 3.5 | 40.7 ± 13.2 |

PHARMACOLOGICAL EXPERIMENT 3

The effects of the compounds of this invention on blood pressure of anesthetized normotensive rats are studied by intravenous injection of the compound.

The blood pressure of rats is monitored via a cannula inserted into the femoral artery by a transducer.

The results thus obtained are summarized in Table 4.

TABLE 4

| Compound No. | Dose (mg/kg) | Decrease in blood Pressure (mm Hg) |
|---|---|---|
| 1 | 1 | 36.6 ± 7.4 |
| 14 | 1 | 39.0 ± 11.6 |
| 19 | 1 | 29.4 ± 5.9 |

PHARMACOLOGICAL EXPERIMENT 4

The mode of vasorelaxing action of the compound of this invention is further studied accrding to method of S. Shibata et al. (European Journal of Pharmacology, 99 (1984) 219–226) using guinea pig aorta. In FIG. 1, the residual contractions induced by norepinephrine ($10^{-4}M$) in $Ca^{++}$—free medium in the presence of various drugs are shown. The known $Ca^{++}$—antagonists such as nifedipine, rerapamil and diltiazem can not suppress this contraction, but compound 14 suppresses it, dose-dependently.

ACUTE TOXICITY

The acute toxicity of the compounds of this invention in mice per os is as follows.

TABLE 5

| Compound No. | $LD_5$ (mg/kg) |
|---|---|
| 1 | 868 |
| 14 | 1420 |
| 19 | 1310 |

The following examples illustrate the synthetic procedure to give the compound of this invention. It should be understood, however, that this invention is not limited solely to the particular examples given below.

EXAMPLE 1

Process 1

5-Bromoacetyl-2,3,4,5-tetrahydro-1,5-benzothiazepine

To a solution of 7.63 g of 2,3,4,5-tetrahydro-1,5-benzothiazepine in 90 ml of toluene and 4.34 g of pyridine, is added a solution of 11.2 g of bromoacetylbromide in 40 ml of toluene dropwise during cooling in ice water with stirring. Then it is stirred continuously for 30 min. at temperature of 3°–5° C., then stirred at room temperature for 2 hours. The reaction mixture is filtered and the residue is washed with a small amount of toluene. Filtered and washed toluene is washed with a saturated sodium chloride solution and dried over anhydrous sodium sulfonate and then toluene is removed under reduced pressure. The residue (12.2 g) is recrystallized in ethanol to give the objective substance (10.98 g).

m.p.: 114°–116° C.
M.S. (m/e): 286 (M+).
I.R. (KBr): 2920, 2900, 1655, 1570 $cm^1$.

Process 2

5-[2-(2-Hydroxypropylamino)-1-acetyl]-2,3,4,5-tetrahydro-1,5-benzothiazepine

To a solution of 0.5 g of N-bromoacetyl-2,3,4,5-tetrahydrobenzothiazepine in 1.5 ml of dichloromethane is added 0.29 g of 1-amino-2-propanol and the resulting solution is refluxed for 8 hours. After complete reaction, 10 ml of dichloromethane is added to the reaction mixture and the mixture is washed with a saturated sodium chloride solution and dried over anhydrous sodium sulfonate. The resultant crystals after removal of dichloromethane are washed with petroleum ether, thus yielding 0.33 g of the objective compound.

m.p.: 105°–108° C.
M.S. (m/e): 280 (M+).
I.R. (KBr): 3360, 2950, 2980, 1640, 1465 $cm^1$.

EXAMPLE 2–16

The compounds from No. 2 to No. 16 are obtained by reacting a compound shown in column A of Table 6 which was obtained according to process 1 of Example 1 with a compound in column B of Table 6 in the process 2 of Example 1.

TABLE 6

| Example No. | A (benzothiazepine with $O=C-(CH_2)_n-Br$) n | B  H—Z  —Z | Compound No. | m.p. °C. | M.S. (m/e) |
|---|---|---|---|---|---|
| 2 | 1 | $-NH-C(CH_3)(CH_3)-CH_2OH$ | 2 | 87–89 | 294 (M+) |
| 3 | 1 | $-N$(piperidine) | 3 | 67–68 | 290 (M+) |
| 4 | 1 | $-NH-$(6-methylpyridin-2-yl) | 4 | 145–146 | 312 (M+) |

TABLE 6-continued

Structure: 2,3,4,5-tetrahydro-1,5-benzothiazepine with N-substituent $O=C-(CH_2)_n-Br$ (labeled A), and B = H-Z / -Z

| Example No. | A n | B -Z | Compound No. | m.p. °C. | M.S. (m/e) |
|---|---|---|---|---|---|
| 5 | 1 | -N(CH(CH₃)₂)₂ | 5 | 98–99 | 306 (M⁺) |
| 6 | 1 | -NH-C₆H₅ | 6 | 119–121 | 298 (M⁺) |
| 7 | 1 | -NH(CH₂)₃-N(CH₃)₂ | 7 | | 307 (M⁺) |
| 8 | 1 | -NH(CH₂)₃-N(C₂H₅)₂ | 8 | oily substance | 321 (M⁺) |
| 9 | 1 | -N-(4-(4-chlorophenyl)-4-hydroxypiperidinyl) | 9 | 139–140 | 416 (M⁺) |
| 10 | 1 | -N(piperazinyl)-C₆H₅ | 10 | 103–104 | 367 (M⁺) |
| 11 | 1 | -NH-(CH₂)₂-(3,4-dimethoxyphenyl) | 11 | 75–76 | 386 (M⁺) |
| 12 | 1 | -N(CH₃)-C₆H₅ | 12 | 140–143 | 312 (M⁺) |
| 13 | 2 | -N(4-methylpiperazinyl) | 13 | 81–83 | 319 (M⁺) |
| 14 | 2 | -NH-(CH₂)₂-(3,4-dimethoxyphenyl) (fumaric acid salt) | 14 | 68–72 | 400 (M⁺) |
| 15 | 2 | -NH-CH₂-CH(OH)-CH₃ | 15 | 95–97 | 294 (M⁺) |

TABLE 6-continued

| Example No. | n | —Z | Compound No. | m.p.°C. | M. S. (m/e) |
|---|---|---|---|---|---|
| 16 | 2 | —NH—CH$_2$CH$_2$—C$_6$H$_5$ | 16 | 81–83 | 340 (M+) |

EXAMPLE 17

5-[2-[4-(p-chlorophenyl)-4-hydroxypiperidino]ethyl]-2,3,4,5-tetrahydro-1,5-benzothiazepine (compound 17)

1.2 g of compound of example 9, 5-[2-[4-(p-chlorophenyl)-4-hydroxypiperidino-]-1-acetyl]-2,3,4,5-tetrahydro-1,5-benzothiazepine is dissolved in 30 ml of anhydrous ether, then 0.327 g of lithium aluminum hydride is added to this solution. After 30 hours' reflux to the reaction mixture is added a small amount of saturated ammonium chloride under cooled conditions with in an ice-water bath, then Celite is added. To remove this Celite, the mixture is filtered. The aqueous layer is extracted with ether. The ether layer thus obtained is washed with a saturated sodium chloride solution, dried over anhydrous sodium sulfonate and concentrated under reduced pressure. The residue is recrystallized with ether, giving 0.24 g of the objective substance.

m.p.: 95°–98° C.
M.S. (m/e): 402 (M+).
I.R. (KBr): 3700, 3360, 2920, 2800, 1570, 1470 cm$^1$.

EXAMPLE 18 AND 19

Reducing compounds 1 and 11 which were obtained by Example 1 and Example 11 by the same procedure of Example 17 will give the compounds 18 and 19.

Compound 18

5-[2-(2-Hydroxypropylaminoethyl]-2,3,4,5-tetrahydro-1,5-benzothiazepine
Oily substance
M.S. (m/e): 266 (M+).

Compound 19

5-[2(3,4-Dimethyoxyphenethylaminoethyl)]-2,3,4,5-tetrahydro-1,5-benzothiazepine
Oily substance
M.S. (m/e): 372 (M+).

EXAMPLE 20

N-[2(N'-acetyl-N'-β-phenethylamino)-1-acetyl]-2,3,4,5-tetrahyddro-1,5-benzothiazepine (Compound 20)

To a solution of 0.5 g. of N-[2-(N'-β-phenethylamino)-1-acetyl]-2,3,4,5-tetrahydro-1,5-benzothiazepine in 7 ml of benzene, is added 0.2 g of acetyl chloride is dropwise and then is added 0.17 g of triethylamine under cooled conditions in an ice-water bath. Then the mixture solution is reacted at room temperature by stirring overnight. The reaction mixture is then poured in ice-water and extracted with benzene. The benzene layer is washed with a saturated sodium sulfonate solution and dried. The residue after removal of benzene is recrystallized from benzene to give 0.25 g of the objective substance.

m.p.: 163°–166° C.
M.S. (m/e): 369 (M++1).
I.R. (KBr): 3450, 1660, 1640, 1470 cm$^{-1}$.

EXAMPLE 21

N-[2-(N'-Propionyl-N'-β-phenethylamino)-1-acetyl]-2,3,4,5-tetrahydro-1,5-benzothiazepine (Compound 21)

The same procedure of example 20 is applied, using propionyl chloride instead of acetyl chloride to give the objective substance.

m.p.: 156°–158° C.
M.S. (m/e): 384 (M++1).

The following examples illustrate a few pharmaceutical dosage unit compositions comprising the compound of the present invention as an active ingredient. The parts given below are by weight.

EXAMPLE 22

(Tablet)

Compound 14, 50 parts
Lactose, 30 parts
Crystalline cellulose, 56 parts
Calcium stearate, 4 parts Preparation The ingredients are intimately admixed with each other, and the resulting mixture is compressed into 150 mg-tablets in a conventional manner.

EXAMPLE 23

(Capsules)

Capsule fillers having the same compositions as example 22 are filled into gelatin capsules of a suitable size in a conventional manner.

EXAMPLE 24

(Granules)

Compound 16, 50 parts
Lactose, 80 parts
Cornstarch, 26 parts
Methyl cellulose, 4 parts Preparation The admixed ingredients of compound 16, lactose and cornstarch are granulated using a methyl cellulose solution and dried to make granules.

EXAMPLE 25

(Syrup)

Compound 19, 2 parts
Sugar, 25 parts
Citric acid, 1 parts
Methyl cellulose, 0.5 parts
Methyl-paraben, 0.05 parts
Vanilla, 0.01 parts The ingredients are suspended in 100 parts of water in a conventional manner.

What we claim is:

1. A compound of the formula:

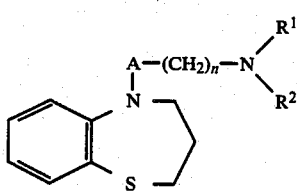

wherein:
A is $>C=O$ or $>CH_2$;
n is an integer from 1 to 3;
$R^1$ is H, a lower alkyl or lower alkanoyl group; and
$R^2$ is a phenyl group, a pyridyl or lower alkyl substituted pyridyl group, the group

—R—OH wherein R is a lower alkyl group, the group

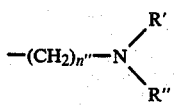

wherein R' and R" each represent a lower alkyl group and n" is 1 or 2, or the group —CH$_2$CH$_2$—Ph, wherein Ph is a phenyl group or phenyl group substituted with lower alkoxy or chloro groups n' is 1 or 2; or a pharmaceutically acceptable acid addition salt thereof.

2. The compound according to claim 1, wherein $R^1$ is hydrogen.
3. The compound according to claim 1 wherein B is $R^2$ is —CH$_2$CH$_2$—Ph.
4. The compound according to claim 1, wherein $R^1$ is hydrogen and $R^2$ is —CH$_2$CH$_2$—Ph.
5. The compound according to claim 1, wherein $R^1$ is hydrogen and $R^2$ is —CH$_2$CH$_2$—Ph, wherein Ph is a phenyl or methoxy-substituted phenyl group.
6. The compound according to claim 1, wherein A is $>C=O$ and n is 1 or 2.
7. The compound according to claim 1, wherein A is $>C=O$, B is $R^1$ is hydrogen and $R^2$ is —CH$_2$CH$_2$Ph.
8. The compound according to claim 1, wherein n is 1 or 2, $R^1$ is hydrogen and $R^2$ is —CH$_2$CH$_2$Ph.
9. The compound according to claim 1 which is 5-[3-(3,4-dimethoxy-β-phenylethylamino)-1-propionyl]-2,3,4,5-tetrahydro-1,5-benzothiazepine.
10. The compound according to claim 1 which is 5-[3-(β-phenethylamino)-1-propionyl]-2,3,4,5-tetrahydro-1,5-benzothiazepine.
11. The compound according to claim 1 which is 5-[2-(3,4-dimethoxy-β-phenylethylamino)-1-ethyl]-2,3,4,5-tetrahydro-1,5-benzothiazepine.
12. The compound according to claim 1 which is 5-[2-(2-hydroxypropylamino)-1-acetyl]-2,3,4,5-tetrahydro-1,5-benzothiazepine.
13. The compound according to claim 1 in which $R^2$ is

14. The compound according to claim 1 wherein $R^2$ is —CH$_2$CH$_2$—Ph.
15. The compound according to claim 1 wherein Ph is a phenyl or lower alkoxyphenyl group.
16. The compound according to claim 1 wherein Ph is a phenyl or methoxyphenyl group.
17. A therapeutic composition to inhibit hypertension comprising a pharmaceutically acceptable carrier and as an active ingredient a compound defined in claim 1 in an amount effective to inhibit hypertension.

* * * * *